(12) United States Patent
Ritter et al.

(10) Patent No.: US 11,148,092 B2
(45) Date of Patent: Oct. 19, 2021

(54) TEMPERATURE-VACUUM SWING ADSORPTION PROCESS FOR CAPTURE OF CO2

(71) Applicant: UNIVERSITY OF SOUTH CAROLINA, Columbia, SC (US)

(72) Inventors: James A. Ritter, Gilbert, SC (US); Armin D. Ebner, Lexington, SC (US); Charles E. Holland, Cayce, SC (US)

(73) Assignee: University of South Carolina, Columbia, SC (US)

( * ) Notice: Subject to any disclaimer, the term of this patent is extended or adjusted under 35 U.S.C. 154(b) by 316 days.

(21) Appl. No.: 16/454,972

(22) Filed: Jun. 27, 2019

(65) Prior Publication Data

US 2020/0001225 A1    Jan. 2, 2020

Related U.S. Application Data

(60) Provisional application No. 62/690,471, filed on Jun. 27, 2018.

(51) Int. Cl.
*B01D 53/047*    (2006.01)
*B01D 53/04*    (2006.01)
(Continued)

(52) U.S. Cl.
CPC .......... *B01D 53/0462* (2013.01); *A01G 7/02* (2013.01); *A01G 33/00* (2013.01);
(Continued)

(58) Field of Classification Search
CPC .. A01G 33/00; A01G 7/02; B01L 5/02; B01L 7/00; B01L 2300/105; B01L 2300/1805;
(Continued)

(56) References Cited

U.S. PATENT DOCUMENTS 2,944,627 A       7/1960  Skarstrom
4,233,038 A  *  11/1980  Tao ........................... C07C 7/13
                                                                          95/104
(Continued)

FOREIGN PATENT DOCUMENTS

EP         0904825         3/1999
EP         1221337         7/2002
(Continued)

OTHER PUBLICATIONS

Aaron, et al. "Separation of $CO_2$ from flue gas: a review" *Sep. Sci. Tech.* 40 (2005) pp. 321-348.
(Continued)

*Primary Examiner* — Frank M Lawrence, Jr.
(74) *Attorney, Agent, or Firm* — Dority & Manning, P.A.

(57) ABSTRACT

Methods and systems for capture of $CO_2$ from a hydrated gaseous stream are described. Systems can be utilized for direct air capture of $CO_2$ and incorporate a low energy temperature-vacuum swing adsorption (TVSA) process. A TVSA process can include a multi-step $CO_2$ capture bed regeneration process that includes depressurization of the bed, heating of the bed, venting and purging of the bed, and cooling of the bed. Multiple beds can be cycled between $CO_2$ capture and regeneration, during which captured $CO_2$ is recovered. Off-gas from a $CO_2$ capture bed can be used in regenerating a parallel bed for increased efficiency.

20 Claims, 6 Drawing Sheets

(51) Int. Cl.
*B01D 53/26* (2006.01)
*C12M 1/00* (2006.01)
*B01L 5/02* (2006.01)
*B01L 7/00* (2006.01)
*A01G 7/02* (2006.01)
*A01G 33/00* (2006.01)

(52) U.S. Cl.
CPC ....... *B01D 53/0476* (2013.01); *B01D 53/261* (2013.01); *B01L 5/02* (2013.01); *B01L 7/00* (2013.01); *C12M 23/18* (2013.01); *B01D 2256/22* (2013.01); *B01D 2257/504* (2013.01); *B01D 2257/80* (2013.01); *B01D 2259/404* (2013.01); *B01D 2259/40049* (2013.01); *B01D 2259/40052* (2013.01); *B01D 2259/40069* (2013.01); *B01D 2259/40081* (2013.01); *B01L 2300/105* (2013.01); *B01L 2300/1805* (2013.01); *B01L 2400/049* (2013.01)

(58) Field of Classification Search
CPC .......... B01L 2400/049; B01D 53/0462; B01D 53/0476; B01D 53/261; B01D 2256/22; B01D 2257/504; B01D 2257/80; B01D 2259/40003; B01D 2259/40013; B01D 2259/4002; B01D 2259/40028; B01D 2259/40049; B01D 2259/40052; B01D 2259/40069; B01D 2259/40075; B01D 2259/40081; B01D 2259/404; B01D 2259/414; C12N 1/12; C12M 23/18; C12M 47/18; Y02C 20/40; Y02P 20/59; Y02P 60/20
USPC ...... 95/96–99, 102, 114, 115, 117, 121, 122, 95/139; 96/121, 122, 126, 130, 131, 132, 96/143, 144, 146
See application file for complete search history.

(56) References Cited

U.S. PATENT DOCUMENTS

| | | | |
|---|---|---|---|
| 4,472,178 A * | 9/1984 | Kumar | B01D 53/0462 95/99 |
| 4,726,815 A | 2/1988 | Hashimoto et al. | |
| 4,784,672 A * | 11/1988 | Sircar | B01J 20/3466 95/97 |
| 4,840,647 A | 6/1989 | Hay | |
| 4,892,565 A | 1/1990 | Schmidt et al. | |
| 4,915,711 A | 4/1990 | Kumar | |
| 5,026,406 A | 6/1991 | Kumar | |
| 5,248,322 A | 9/1993 | Kumar | |
| 5,354,346 A | 10/1994 | Kumar | |
| 5,779,767 A | 7/1998 | Golden et al. | |
| 5,914,455 A * | 6/1999 | Jain | B01D 53/0462 95/96 |
| 5,917,136 A | 6/1999 | Gaffney et al. | |
| 6,245,127 B1 | 6/2001 | Kane et al. | |
| 6,322,612 B1 | 11/2001 | Sircar et al. | |
| 6,454,838 B1 | 9/2002 | Xu et al. | |
| 7,384,574 B2 | 6/2008 | Zidan et al. | |
| 8,153,554 B2 | 4/2012 | Ritter et al. | |
| 9,016,084 B2 | 4/2015 | Alden et al. | |
| 2005/0032641 A1 | 2/2005 | Ritter et al. | |
| 2009/0142258 A1 | 6/2009 | Ritter et al. | |
| 2011/0218099 A1 | 9/2011 | Ritter et al. | |
| 2012/0324931 A1 | 12/2012 | Alden et al. | |
| 2014/0370576 A1 | 12/2014 | Wright et al. | |

FOREIGN PATENT DOCUMENTS

| | | |
|---|---|---|
| WO | WO 2009/073928 | 6/2009 |
| WO | WO 2009/126607 | 10/2009 |

OTHER PUBLICATIONS

Bhadra, et al. "On the Use of the Dual Process Langmuir Model for Predicting Unary and Binary Isosteric Heats of Adsorption" *Langmuir* 28 (2012) pp. 6935-6941.
Brown, et al. "Using Krylov Methods in the Solution of Large Scale Differential-Algebraic Systems" *SIAM J. Stat. Comp.* 15 (1994) pp. 1467-1488.
Cen, et al. "Bulk gas separation by pressure swing adsorption" *Ind. Eng. Chem. Fundam.* 25(4) (1986) pp. 758-767.
Ebner, et al. "Graphical Unit Block Approach for Complex PSA Cycle Scheduling of Parallel Interacting Trains of Columns and Tanks" 21 *Adsorption* (2015) pp. 229-241.
Ebner, et al. "Graphical Approach for Complex PSA Cycle Scheduling" *Adsorption* 15 (2009) pp. 406-421. (Abstract only).
Ebner, et al. "State-of-the-Art Adsorption and Membrane Separation Processes for Carbon Dioxide Production from Carbon Dioxide Emitting Industries" *Separation Science and Technology* 44 (2009) pp. 1273-1421.
Epa. "Emissions & Generation Resource Integrated Database (eGRID)" *U.S. Environmental Protection Agency* (2007).
Erden, et al. "Development of a Pressure Swing Adsorption Cycle for Producing High Purity CO2 from Dilute Feed Streams. Part I: Feasibility Study" *Ind. Eng. Chem. Res.* 57 (2018) pp. 8011-8022.
Erden, H. "Two-Stage PSA System for $CO_2$ Removal and Concentration During Closed-Loop Human Space Exploration Missions" *U. S. Carolina* (2016) pp. 1-213.
Fenske, et al. "Human Breath Emissions of VOCs" *J. Air & Waste Manage. Assoc.* 49 (1999) pp. 594-598.
Griffiths, et al. "Area of Interest B2: Bench-Scale Development and Testing of Rapid PSA for $CO_2$ Capture" *US Dept. of Energy* DE-FOA-0000403 (2011) pp. 1-74.
Iea. "World Energy Outlook" *Intl. Energy Agency* (2009) pp. 1-698.
Knox, et al. "Integrated Test and Evaluation of a 4-Bed Molecular Sieve (4BMS) Carbon Dioxide Removal System (CDRA), Mechanical Compressor Engineering Development Unit (EDU), and Sabatier Engineering Development Unit (EDU)" *Intl Conf Eriviron Sys* (2005).
Kohl, et al. "Gas Purification" *Gulf Publishing Company* (1997) pp. 1-1409.
Lee, et al. "A Review on Solid Adsorbents for Carbon Dioxide Capture" *J Indust Eng Chem* 23 (2015) pp. 1-11.
Li, N.N. "Recent Developments in Separation Science" *CRC Press* (1972).
Liu, et al. "Pressure Swing Adsorption-Solvent Vapor Recovery: Process Dynamics and Parametric Study" *Ind. Eng. Chem. Res.* 35 (1996) pp. 2299-2312.
Mehrotra, et al. "Arithmetic Approach for Complex PSA Cycle Scheduling" *Adsorption* 16 (2010) pp. 113-126.
Mohammadi, et al. "New PSA Cycle Schedules for Producing High Purity Oxygen Using Carbon Molecular Sieve" *Ind. Eng. Chem. Res.* 55 (2016) pp. 10758-10770.
Reynolds, et al. "Heavy Reflux PSA Cycles for $CO_2$ Recovery from Flue Gas. Part I. Performance Evaluation" *Adsorption* 14 (2008) pp. 399-413.
Riboldi, et al. "Overview on Pressure Swing Adsorption (PSA) as $CO_2$ Capture Technology: State-of-the-Art, Limits and Potentials" *Energy Procelia* 114 (2017) pp. 2390-2400.
Ritter, et al. "Hybrid Adsorption Process and Flow Sheet for $CO_2$ Capture from Flue Gas" *U. S. Carolina* (2014) pp. 1-42.
Ritter, et al. "On the Use of the Dual Process Langmuir Model for Correlating Unary and Predicting Mixed Gas Adsorption Equilibria" *Langmuir* 27 (2011) pp. 4700-4712.
Ruthven, et al. "Swing Adsorption" *VCH Publishers* (1994).
Samanta, et al. "Post-Combustion ($CO_2$ Capture Using Solid Sorbents: A Review" *Ind. Eng. Chem. Res.* 51 (2012) pp. 1438-1463.
Sanz-Perez, et al. "Direct Capture of $CO_2$ from Ambient Air" *Chem. Rev.* 116 (2016) pp. 11840-11876.
Subramanian, et al. "Equilibrium Theory for Solvent Vapor Recovery by Pressure Swing Adsorption: Analytic Solution for Process Performance" *Chem. Eng. Sci.* 52 (1997) pp. 3147-3160.

(56) References Cited

OTHER PUBLICATIONS

Xiao, et al. "Capture of $CO_2$ from flue gas streams with zeolite 13X by vacuum pressure swing adsorption" *Adsorption* 14 (2008) pp. 575-582.

Zhang, et al. "Effect of flue gas impurities on $CO_2$ capture performance from flue gas at coal-fired power stations by vacuum swing adsorption" *Energy Procedia* 1 (2009) pp. 1115-1122.

Zhang, et al. "Effect of process parameters on power requirements of vacuum swing adsorption technology for $CO_2$ capture from flue gas" *Energy Con. Manag.* 49 (2008) pp. 346-356. (Abstract only).

\* cited by examiner

| Valve | Half Cycle 1 | | | | | | | Half Cycle 2 | | | | | | |
|---|---|---|---|---|---|---|---|---|---|---|---|---|---|---|
| | FI | CnD | IH | HV | HP | CP | SI | FI | CnD | IH | HV | HP | CP | SI |
| 1 | x | x | x | x | X | x | x | | | | | | | |
| 2 | | | | | | | | x | x | x | x | x | x | x |
| 3 | | | | | | | | x | x | x | x | x | x | x |
| 4 | x | x | x | x | X | x | x | | | | | | | |
| 5 | x | x | x | x | X | x | x | | | | | | | |
| 6 | | | | | | | | x | x | x | x | x | x | x |
| 7 | | | | | | | | x | x | x | x | x | x | x |
| 8 | x | x | x | x | X | x | x | | | | | | | |
| 9 | x | x | x | x | X | x | x | | | | | | | |
| 10 | | | | | | | | x | x | x | x | x | x | x |
| 11 | | | | | | | | x | | x | x | x | | |
| 12 | | x | | x | X | x | | | | | | | | |
| 13 | x | x | x | x | X | x | x | | | | | | | |
| 14 | | | | | | | | x | x | x | x | x | x | x |
| 15 | | | | | | | | | | | | x | x | |
| 16 | | | | X | x | | | | | | | | | |
| 17 | | | | X | | | | | | | | x | | |
| 18 | x | x | x | x | X | | x | x | x | x | x | x | | x |
| 19 | | | | x | X | | | | | | | x | x | |
| 20 | x | x | x | | | x | x | x | x | x | | | x | x |
| 21 | | x | | | | | | | x | | | | | |
| 22 | | | | | | x | | | | | | | x | |
| 23 | | | | | | x | | | | | | | x | |
| 24 | x | x | x | x | X | x | x | | | | | | | |

FIG. 4

| C1 | Feed | | | | | | | I | CnD | IH | HV | HP | CP | I |
|---|---|---|---|---|---|---|---|---|---|---|---|---|---|---|
| C2 | I | CnD | IH | HV | HP | CP | I | Feed | | | | | | |
| T1 | | | TP | | | | | | | TP | | | | |
| | Day | | | | | | | Night | | | | | | |
| t | t1 | t2 | t3 | t4 | t5 | t6 | t7 | t1 | t2 | t3 | t4 | t5 | t6 | t7 |

TEMPERATURE-VACUUM SWING ADSORPTION PROCESS FOR CAPTURE OF CO2

CROSS REFERENCE TO RELATED APPLICATION

This application claims filing benefit of U.S. Provisional Patent Application Ser. No. 62/690,471, having a filing date of Jun. 27, 2018, which is incorporated herein by reference for all purposes.

BACKGROUND

The removal of carbon dioxide ($CO_2$) from gas streams has traditionally been utilized to purify other components of the source gas stream, e.g., hydrogen ($H_2$), in steam methane reforming, methane in natural gas purification, etc. The removal of metabolic $CO_2$ from air has also been of interest for many years, particularly with the advent of human space flight and underwater exploration. For instance, considerable effort has been put forth by NASA to remove metabolic $CO_2$ from spacecraft cabin air.

Removal of $CO_2$ from gas streams combined with the capture of the isolated $CO_2$ has become of increasing interest in recent years, as $CO_2$ released from transportation, industrial processes, and the electric power industry has been implicated and widely accepted as being a cause of climate change. Moreover, as improved methods for utilization of high purity $CO_2$ have been developed—for instance, in green technologies as a fuel source, as an extraction solvent, and in algae and plant cultivation—the gas separations industry has shown great interest in improving methodologies for separating and capturing $CO_2$ from $CO_2$-containing gases, including direct capture from the air.

Adsorption technology, especially temperature-vacuum swing adsorption (TVSA), has been proposed and studied extensively for $CO_2$ capture. Gas separation by TVSA is achieved by coordinated pressure and temperature cycling and flow reversals over an adsorbent bed that preferentially adsorbs a component of the mixture, e.g., $CO_2$. Traditionally, TVSA has been utilized to supply high oxygen content streams, e.g., medical oxygen. TVSA has also been utilized in the removal of $CO_2$ as the final step in hydrogen synthesis for use in oil refineries, in the production of ammonia ($NH_3$), in the removal of hydrogen sulfide ($H_2S$) from hydrogen feed and recycle streams of hydrotreating and hydrocracking units, as well as in the separation of $CO_2$ from biogas so as to increase the methane ($CH_4$) ratio.

Unfortunately, conventional TVSA processes make inefficient use of applied energy, and as such, have remained economically unfeasible, particularly when considering separation of $CO_2$ from a hydrated gas stream such as air.

What are needed in the art are systems and methods that can provide for improved separation of $CO_2$ from a gas stream, and in particular from a gas stream that also includes an amount of water vapor. Methods that can provide high purity $CO_2$ from a hydrated feed stream—for instance, directly from air—could be particularly beneficial in green technologies such as algae production.

SUMMARY

According to one embodiment, disclosed is a multi-bed method for separating $CO_2$ from a gaseous stream containing $CO_2$ and water vapor ($H_2O$). A method can include providing a gaseous stream to a first set of beds that includes a first desiccant bed and a first $CO_2$ capture bed. The gaseous stream is fed to the first desiccant bed to form a dry gas stream. The dry gas stream thus formed then flows to the first $CO_2$ capture bed, within which $CO_2$ is preferentially adsorbed, so as to form a dry, low $CO_2$-content gas stream. The method also includes regenerating a second set of beds by removal of $H_2O$ and $CO_2$ from the second set of beds simultaneous with removal of $H_2O$ and $CO_2$ from the gaseous feed by use of the first set of beds. More specifically, a method can include regenerating a second desiccant bed with at least a portion of the dry, low $CO_2$-content gas stream that exits the first $CO_2$ capture bed. In addition, the method includes regenerating a second $CO_2$ capture bed. The regeneration of the second $CO_2$ capture bed is a multi-step TVSA process that includes depressurization of the second $CO_2$ capture bed, heating of the bed to encourage desorption of $CO_2$ previously adsorbed in the bed, venting of the $CO_2$ capture bed, and purging and cooling of the $CO_2$ capture bed. The purge gas used during purging steps of the regeneration process can include a portion of the dry, low $CO_2$-content gas stream that exits the first $CO_2$ capture bed. Optionally, a portion of the purge gas can also be used in regeneration of the second desiccant bed.

The method can be a cyclic, continuous method, and upon completion of the regeneration of the second desiccant and $CO_2$ capture beds, this second set of beds can be utilized to remove $H_2O$ and $CO_2$ from a feed gas, while the first set of beds is regenerated by use of the dry, low $CO_2$-content stream coming off of the second $CO_2$ capture bed.

$CO_2$ that is pulled off of the $CO_2$ capture beds during the venting and purging steps of the $CO_2$ capture bed regeneration process can be used directly or can be collected, stored, transported, etc. For instance, in one embodiment, the cycles can be timed and controlled so as to deliver $CO_2$ semi-continuously over the course of a day (e.g., during daylight hours), which can be used to encourage growth and development of an ecological system, e.g., in algae or plant growth.

Also disclosed are systems that can be used for carrying out the $CO_2$ capture methods. For instance, a system can include a first and second desiccant bed and a first and second $CO_2$ capture bed. A system can also include suitable valving and piping such that the light product ends of the first and second desiccant beds are in controllable fluid communication with the heavy product ends of the first and second $CO_2$ capture beds, respectively, and also such that the light product end of the first $CO_2$ capture bed is in controllable fluid communication with the light product end of the second desiccant bed and also with the light product end of the second $CO_2$ capture bed for controlled countercurrent flow through these beds during the bed regeneration process. Likewise, the light product end of the second $CO_2$ capture bed can be in controllable fluid communication with the light product end of the first desiccant bed and also with the light product end of the first $CO_2$ capture bed for controlled countercurrent flow through these beds during the bed regeneration process for the first set of beds. The system can also include one or more vacuum pumps in controllable fluid communication with the heavy product ends of the first and second $CO_2$ capture beds (for countercurrent depressurization of the capture beds), heaters for heating the capture beds, a storage tank for storage/pressurization of $CO_2$ removed by use of the system, and other control and flow components as further described herein.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed is a method and system for capture of $CO_2$ from a hydrated gaseous stream. In one particular embodiment, the system can be utilized for direct air capture (DAC) of $CO_2$. The system utilizes a low energy temperature-vacuum swing adsorption (TVSA) process and includes multiple desiccant beds for the removal of water vapor and multiple capture beds for the capture and concentration of $CO_2$. Optionally, a system can also include a storage/delivery tank for storing the concentrated $CO_2$.

Disclosed systems can be utilized to capture $CO_2$ from hydrated streams for direct use, for storage, for transportation, or for any combination thereof. For instance, as one application example, a system can be utilized to produce $CO_2$ for use in algae production, which is of increasing interest for use in green fuel production, as well as food production. Utilization of disclosed systems can make such applications affordable and environmentally sustainable, particularly when combined with renewable heat and energy sources, and integrated with an efficient $CO_2$ delivery technology for optimized $CO_2$ utilization.

Disclosed systems utilize multiple adsorption beds operating in series (as a set of adsorption beds) and parallel with one another such that while one set of beds is processing a feed stream to remove $CO_2$ and $H_2O$ from the feed stream, another parallel set of beds is being regenerated to remove captured $CO_2$ and $H_2O$ from the beds. Moreover, the dry, $CO_2$-depleted gas that exits one set of beds can be utilized in the regeneration of another set of beds. In addition, the regeneration of the $CO_2$ capture beds of the system can be carried out according to a highly efficient, multi-step TVSA process. As such, the overall process can be continuous, highly efficient, and economically feasible.

Figure 1:
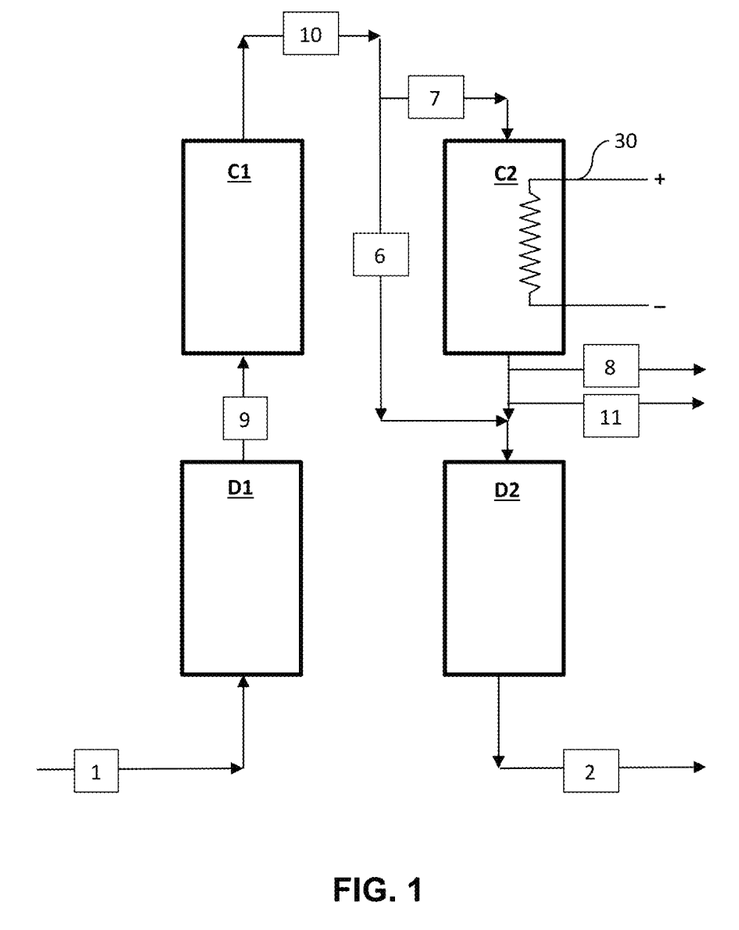
FIG. 1 illustrates flow through a four-bed $CO_2$ capture system during a first half of a cycle.

FIG. 1 schematically illustrates flow through a system that includes two sets of adsorption beds during one half of an adsorption cycle. As shown, the illustrated system includes a first set of adsorption beds that includes a first desiccant bed D1 and a first $CO_2$ capture bed (also referred to herein as simply a capture bed) C1 and also includes a second set of adsorption beds that includes a second desiccant bed D2 and a second capture bed C2.

While the embodiment illustrated in FIG. 1 and much of the following discussion describes a system that includes two sets of adsorption beds, each including a desiccant bed and a capture bed, it should be understood that the systems and methods disclosed herein are not limited to those that incorporate two sets of adsorption beds or to systems in which each set of adsorption beds includes only a single desiccant bed and a single capture bed. In particular, systems encompassed herein can include multiple sets of adsorption beds that can operate in conjunction with or independently of one another and each set of adsorption beds can include beds in addition to a single desiccant bed and a single $CO_2$ capture bed. For instance, a set of adsorption beds can include one or more additional desiccant beds, one or more additional $CO_2$ capture beds, as well as adsorption beds for other targeted components that may be carried in a gaseous feed stream.

As shown in FIG. 1, during a first half of a cycle, a feed stream 1 can pass through a first desiccant bed D1. The feed pressure and temperature are not particularly limited, and in one embodiment, can be at or near atmospheric pressure (e.g., about 1 atm). For instance, in one embodiment, the feed stream 1 can be air directly fed to the desiccant bed D1 by use of a feed blower, and as such, the feed stream 1 may be slightly above atmospheric pressure. In one embodiment, desiccant bed D1 can operate at ambient temperature. Similarly, the feed flow rate is not particularly limited. By way of a non-limiting example, in one embodiment, a system can process continuously with a feed rate of ambient air of from about 100 SLPM to about 500 SLPM, e.g., about 200 SLPM, which can produce from about 100 g/day to about 500 g/day, e.g., about 200 g/day, of $CO_2$ in a direct air capture application.

The desiccant bed D1 can include any suitable desiccant material in any suitable format for removal of water vapor from the feed stream 1. Desiccant materials can include, for example, inorganic species like zeolites, alumina, and silica gels. Such desiccants can have high water adsorption capacities and favorable water adsorption isotherm shapes. For instance, the water adsorption capacity of the desiccant can be from about 20 wt. % to about 50 wt. %. Use of a high-capacity desiccant can decrease the amount of desiccant necessary for drying, can decrease the size and number of desiccant beds in a system, and can decrease the cycle time for the water vapor removal step of a system. Useful desiccants can also have water adsorption isotherms that are concave to the pressure axis, particularly at low pressure, which can help in forming short, sharp mass transfer zones.

By way of example, in one embodiment, a desiccant bed D1 can include a silica gel or activated alumina and can incorporate a layer of zeolite (e.g., 13X zeolite) in a layered bed format for the removal of water vapor from the feed gas 1.

In general, the desiccant bed D1 can include a packed bed of porous particles that incorporate the desiccant material according to known fashion, but there is no particular form for inclusion of the desiccant in the desiccant bed D1, and any suitable contact methodology for contact between the hydrated feed gas 1 and the desiccant of the desiccant bed D1 is encompassed herein.

Following passage of the feed gas 1 through the desiccant bed D1, a dry gas stream 9 can exit the light product end of the desiccant bed D1 and pass into the heavy product end of the capture bed C1. As utilized herein, the term "heavy product" refers to a stream that is enriched in $CO_2$ and/or that is enriched in $H_2O$, while the term "light product" refers to a stream that is depleted in $CO_2$ and/or $H_2O$. For instance, a light product flow can carry little or no $CO_2$ and/or little or no $H_2O$. Thus, the feed or heavy product end of a bed is that end through which a flow that is relatively high in $CO_2$ or $H_2O$, depending upon the bed type, passes into the bed prior to stripping the $CO_2$ (or $H_2O$) from the stream in the bed and this flow stream will then exit the bed through the light product end of the bed.

The capture bed C1 can incorporate any suitable materials for preferential adsorption and capture of $CO_2$ from the dry gas stream 9. In one embodiment, adsorbents can be low temperature adsorbents (i.e., process conditions at about 100° C. or less), which can decrease the energy requirements of a system. In one embodiment, the capture bed C1 can operate at ambient temperature.

A suitable $CO_2$ adsorbent may be, for example, a zeolite; an activated carbon; an activated alumina; a silica gel; a carbon-based or non-carbon-based molecular sieve; a metal organic framework structure; one or more oxides or hydroxides of alkali or alkaline-earth metals; or a porous structure containing a substance capable of reacting reversibly with $CO_2$ molecules, such as amines, physical solvents, metallic complexing agents, metal oxides or hydroxides, for example.

In one embodiment, low temperature zeolite adsorbents can be utilized. Zeolites are porous crystalline aluminosilicates, whose frame-work consists of interlocking tetrahedrons of $SiO_4$ and $AlO_4$ joined together in various regular arrangements through shared oxygen atoms. They have open crystal lattices containing pores with molecular dimensions, into which molecules can penetrate. The negative charge created by the substitution of an $AlO_4$ tetrahedron for a $SiO_4$ tetrahedron is balanced by exchangeable cations (e.g., $Na^+$, $K^+$, $Ca2^+$, $Mg2^+$), which are located in the channels and cavities throughout the structure. The adsorption and gas separation properties of zeolites are heavily dependent on the size, charge density, and distribution of these cations in the porous structure. Zeolites as may be incorporated in the adsorption beds can include, without limitation, zeolite X (e.g., zeolite 13X), Y, A (e.g., zeolites 4A, 5A), β, ZSM, CHA, and natural zeolites (e.g. ZAPS, ZNT, ZN-19). Zeolites exchanged with alkali or alkali earth cations can be utilized in some embodiments. Examples include, without limitation, Y and X zeolites exchanged with Li, K, Na, Rb, and Cs and cation-exchanged MZSM-5 (M=Li, Na, K, Rb, Cs, H, Ba). Metal organic frameworks (MOFs) constructed from transition metal ions and bridging organic ligands can also be utilized in $CO_2$ adsorption as can carbon-based materials, e.g., porous carbon-based materials (anthracite or fly ash for example), that have been modified to increase surface alkalinity, alkali metal carbonate-based adsorbents, etc.

$CO_2$ and $H_2O$ adsorbents can be provided in the capture bed C1 and the desiccant bed D1, respectively, according to standard practice, e.g., packed particle bed adsorbents, particle coated parallel channel formations or particles trapped in microfibrous mats, optionally provided in combination with other adsorbents in one or more layers within the bed.

In one embodiment, the adsorbent beds can have a relatively high bed density, e.g., up to about 800 $kg/m^3$, up to about 600 $kg/m^3$, or up to about 400 $kg/m^3$ in some embodiments, which can lower the energy requirements and increase throughput for the systems. In other embodiments, the beds can have a relatively low bed density, e.g., about 150 $kg/m^3$ or less, about 200 $kg/m^3$ or less, or about 250 $kg/m^3$ or less in some embodiments.

The particular characteristics of each of the desiccant and capture beds can be varied, with preferred variations depending upon the particular source feed gas to be processed by the systems. For instance, the desiccant bed D1 can have a different bed density as compared to the capture bed C1, depending upon the concentrations of $H_2O$ and $CO_2$ expected in the feed gas 1.

Following passage through the capture bed C1, a dry, low $CO_2$ content stream 10, can exit the light product end of the capture bed C1. The dry, low $CO_2$ content stream 10 is beneficially utilized in recharging of a second set of adsorbent beds D2, C2 of a system, e.g., the two-bed set system of FIG. 1, while the first set of beds D1, C1 is being utilized to capture $CO_2$ from the feed gas. In one embodiment, the desiccant beds, D1, D2 can be identical to one another, incorporating the same adsorbents in the same volumes and bed densities. Likewise, the capture beds C1, C2 can be identical to one another in some embodiments.

As shown in FIG. 1, at least a portion 6 of the dry, low $CO_2$-content stream 10 can be fed to the second desiccant bed D2 in a countercurrent flow. As utilized herein, the term "countercurrent" refers to the direction of flow for a gaseous stream through an adsorbent bed during the cycle portion of a process in which the adsorbed material, i.e., the $H_2O$ or $CO_2$, is removed from the bed and the bed is regenerated. As such, countercurrent flow is opposite to that of the direction of the feed flow during which $H_2O$ and $CO_2$ are adsorbed in the respective beds.

As the dry, low $CO_2$-content stream 6 flows through the desiccant bed D2 in a countercurrent flow water previously adsorbed by the desiccant of the bed can preferentially transfer to the dry stream 6 and be removed from the bed via humid stream 2. A countercurrent flow for recharging of the desiccant bed can be preferred in some embodiments as it can increase efficiency of the recharging flow.

The capture bed C2 is recharged according to a multi-step process, which improves efficiency and $CO_2$ recovery capability of the system, among other benefits. Over the course of the multi-step process, the bed is depressurized, $CO_2$ is desorbed from the adsorption material by heating the bed, the desorbed $CO_2$ is vented and purged from the bed, and the bed is cooled.

The capture bed C2 can be depressurized by use of a countercurrent depressurization (CnD) step, during which a vacuum pump (not illustrated on FIG. 1) can be utilized to decrease the pressure of the capture bed C2 through its heavy product end with its light product end closed.

During the CnD step, the capture bed C2 will reach the lowest pressure of the cycle (discussed in more detail below). The stream 8 leaving the heavy product end of the capture bed C2 during CnD can include primarily $CO_2$ depleted air that remains in the void spaces of the bed during $CO_2$ capture. This stream 8 can be simply vented from the system as a dry, low $CO_2$-content stream or can be further utilized in recharging other beds (e.g., other desiccant beds) of the system.

Following depressurization, the capture bed C2 can be closed and the bed can be heated, e.g., by use of an electrical heater 30 or the like. Heating can be carried out to a targeted temperature (which can vary depending upon the particular adsorption material used), at which temperature the previously captured $CO_2$ can desorb from the bed material. The release of the $CO_2$ from the adsorption material can also cause the pressure within the closed bed to rise, and as such, the pressure inside the capture bed C2 can rise. Generally, the bed C2 will be pressurized to the maximum pressure of the cycle during the heated desorption step.

A hot venting step can follow the heating/desorption step. During the hot venting step, the bed can be opened and, due to the increased pressure in the bed, the released $CO_2$ can spontaneously flow out of the bed via stream 11 to be captured, pressurized, directly used, etc. While the bed C2 is still hot, and to obtain increased recovery of the captured $CO_2$ a purge gas 7 can be fed countercurrently through the capture bed C2 following the initial venting of the bed. As shown, the purge gas 7 can be provided from the dry, low $CO_2$-content stream 10 that exits the capture bed C1. The purged high content $CO_2$ gas can flow out of the bed via stream 11 to be utilized as desired.

The instigation of the flow of the purge gas 7 through the capture bed C2 can stop or decrease the flow rate of the dry, low $CO_2$-content stream 6 to the desiccant bed D2, but this is not a requirement of a system. Depending upon the particular characteristics of a system, upon instigation of the flow of the purge gas 7 to the capture bed C2, the flow of the dry, low $CO_2$-content stream 6 to the desiccant bed D2 can remain the same, can decrease but still maintain a flow, or can be stopped altogether.

Following venting and purging of the captured $CO_2$, the capture bed C2 can be cooled prior to the next half-cycle, during which it will be utilized to capture $CO_2$ from a feed stream. The cooling of the bed can be encouraged by continuation of flow of a purge gas 7 through the bed C2. During this step, however, the bed will not be heated and the purge gas 7 can carry heat from the bed. Upon exit, the now heated, dry, and low $CO_2$ content purge gas can be fed to the second desiccant bed D2 for further recharging of desiccant bed D2, with the humid air thus formed exiting the system as humid flow 2, as shown.

Upon complete recharge of the second set of adsorption beds D2, C2, flow through the system can be modified and a second half-cycle can take place during which the second set of adsorption beds D2, C2 can be used to capture $H_2O$ and $CO_2$ from a feed stream while the first set of adsorption beds D1, C1 are recharged.

Figure 2:
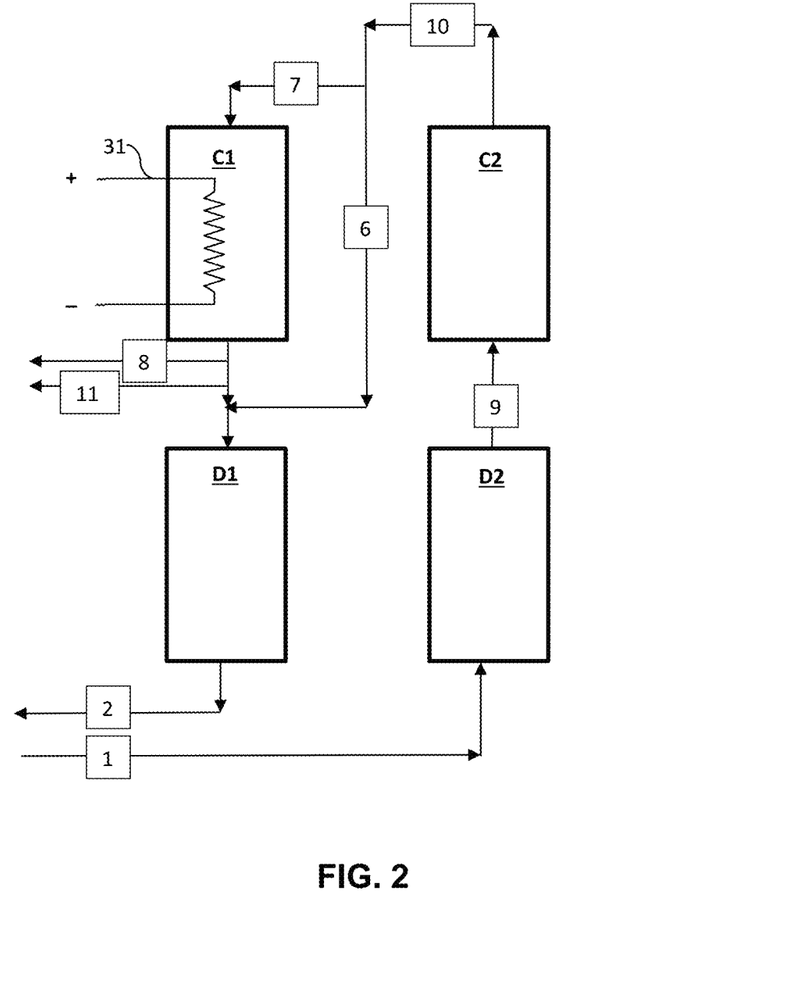
FIG. 2 illustrates flow through the four-bed $CO_2$ capture system of FIG. 1 during the second half of a cycle.

FIG. 2 schematically illustrates this half-cycle. As shown, this half-cycle is essentially identical to the first half-cycle, but the flow through the system simply reversed. Thus, the feed stream 1 is fed to the heavy product end of desiccant bed D2 within which $H_2O$ is removed from the stream such that a dry gas stream 9 exits the light product end of the desiccant bed D2 and enters the heavy product end of the $CO_2$ capture bed C2. As the gas flows through the capture bed C2, $CO_2$ is removed leaving a dry, light product low $CO_2$-content stream 10 to exit the light product end of the capture bed C2.

At least a portion 6 of the dry, low $CO_2$ content stream 10 that exits the capture bed C2 is diverted to the light product end of the desiccant bed D1 and is utilized to remove $H_2O$ and recharge the bed, e.g., in a counter current flow as shown.

At the same time as the dry, low $CO_2$ content stream 6 is utilized to recharge the desiccant bed D1, the capture bed C1 can also be recharged according to the multi-step process as described previously. Specifically, the bed C1 can be subjected to a CnD step, during which the $CO_2$ depleted air held in the bed is vented in a countercurrent flow at 8. Following the CnD step, the bed is closed and heated for instance, by use of an electric heater 31, during which the $CO_2$ desorbs and the pressure in the bed C1 increases. The desorbed $CO_2$ is then removed from the bed via stream 11 by first simply venting and then by use of a hot purge utilizing countercurrent purge gas 7 that is derived from the dry, low $CO_2$ content stream 10. Once the desorbed $CO_2$ is removed from the capture bed C1, the purge gas 7 can be used to cool the bed C1, with the resulting heated, dry, and low $CO_2$-content stream that exits the capture bed C1 being fed to the light product end of the desiccant bed D1 to improve the $H_2O$ removal during the recharging of this bed.

Figure 3:
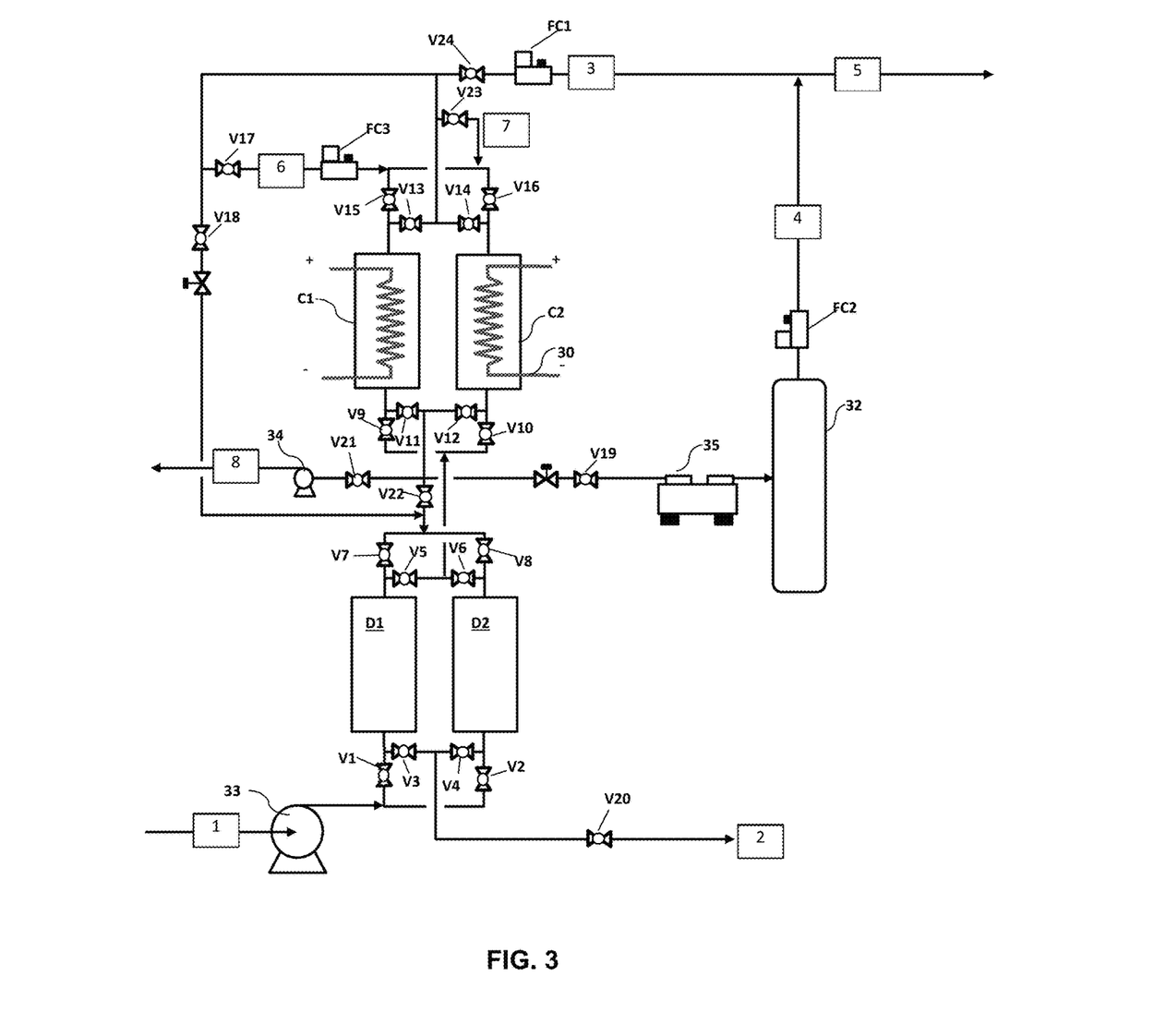
FIG. 3 schematically illustrates one embodiment of a $CO_2$ capture system.

FIG. 3 illustrates one embodiment of a two-bed set system that can be utilized to provide $CO_2$ to a growth system, for instance, to an algae growth pond. In one embodiment, a system can be run so as to provide $CO_2$ to the cultivation area, e.g., an algae growth pond, only during a portion of the day (e.g., daylight hours). By way of example, for a 1,000 L cultivation pond, a system can be designed to continuously process about 200 SLPM of ambient air to produce about 200 g/day of $CO_2$ that can then be delivered to the cultivation pond only during daylight (e.g., over a 12 hr period of the 24 hr day).

To enable the semi-continuous delivery of $CO_2$, the system can include a storage/delivery tank 32. The storage/delivery tank 32 can be replenished with $CO_2$ by repressurization, both during a first period (e.g., during daylight hours) from $CO_2$ obtained during recharging of bed C2, and once during a second period (e.g., night) from $CO_2$ obtained during recharging of bed C1.

During a first half of the cycle, a feed gas 1 (e.g., ambient air containing about 450 ppm of $CO_2$ and about 2 vol. % $H_2O$ vapor) can enter the system with the aid of a feed blower 33 at ambient temperature and a little over 1 atm through valve V1 (valves V2 and V3 closed) into desiccant bed D1. Within bed D1, water can be removed from the feed gas stream. Dry air can then leave desiccant bed D1 through valve V5 (valves V6 and V7 closed) and continue through valve V9 (valves V10 and V11 closed) into $CO_2$ bed C1, wherein $CO_2$ can be adsorbed and thus removed from the now dry gas stream. The dry, low $CO_2$ content gas stream then leaves $CO_2$ bed C1 through valve V13 (valves V14 and V15 closed) and can then be used for regeneration of the $CO_2$ and desiccant beds C2 and D1. In one embodiment, a portion of the dry, low $CO_2$ content gas stream 3 can be used as a diluent for $CO_2$ stream 4 that is pulled out of the storage tank 32. As shown, in this embodiment before $CO_2$ is fed to the cultivation pond via stream 5, a portion 3 of the dry, low $CO_2$ content stream can be combined with the $CO_2$ stream 4, which can be essentially pure $CO_2$ in some embodiments, so as to deliver a predetermined and controlled concentration of $CO_2$ to the cultivation area.

In one embodiment, during the delivery time, e.g., daylight, there can be flow through valve V24 and flow controller FC1 to permit a portion (about 6.5 SLPM in one embodiment) of dry and low $CO_2$ content stream leaving the capture bed C1 through valve V13 to be utilized via stream 3. The remaining fraction of the dry low $CO_2$ content gas stream leaving through valve V13 can be used for bed regeneration, as explained above. Prior to reaching the cultivation area, stream 3 can be blended with stream 4 that is rich in $CO_2$ and coming from the storage/delivery tank 32 through flow controller FC2. By way of example, in one embodiment, a cultivation stream 5 can include about 2 vol. % $CO_2$.

While $H_2O$ and $CO_2$ are being captured in the first desiccant bed D1 and first capture bed C1, second desiccant bed D2 and second capture bed C2 can be regenerated. As discussed above, a multi-step regeneration process for a capture bed can include depressurization, heating, venting, purging, and cooling. In order to align the various steps with available off-gas from another capture bed as well as to align the $CO_2$ recovery with the application use, e.g., cultivation, a process can include one or more idle steps. In addition, the specific time sequence of each step can be designed to maintain desired pressures, bed regeneration rates, $CO_2$, delivery rates and pressures, etc.

By way of example, in one embodiment a $CO_2$ capture bed C2 can undergo a sequence of seven steps that extend over the regeneration portion of a cycle (e.g., a 12 hr period for a two-bed set, 24 hour cycle). These seven regeneration steps can include a first idle (FI) step, a countercurrent depressurization (CnD) step, an idle heating (IH) step, a hot vent (HV) step, a hot purge (HP) step, a cooling purge (CP) step, and a second idle (SI) step. For example, the FI, CnD, and IH steps can occur during the first half of the regeneration period (e.g., 6 hr of a 12 hr regeneration period), and the remaining four steps, i.e., the HV, HP, CP, and SI steps, can occur during the second half of the regeneration period.

The relative timing of each of the steps compared to one another as well as the absolute time period for each step is not required, however, and the timing for each step of a regeneration process can vary depending upon flow rates, bed conditions, feed streams, process application, etc. For instance, when considering the exemplary embodiment, in which $CO_2$ is delivered throughout the day to a cultivation pond, the first three steps of the daylight regeneration process can take place over the first half of the regeneration period so that the storage/delivery tank 32 can be repressurized midway into the day just when it is nearly at its lowest pressure (i.e., nearly atmospheric) to avoid unnecessary over-pressurization. The regeneration process for the desiccant bed D2 can be a more convoluted sequence of regenerations steps that can occur at various times during the regeneration of the capture bed, so as to optimize recovery of $CO_2$ from the capture bed as well as efficiency of the overall process.

By way of example, and without limitation, in one embodiment, when considering a 24-hour cycle including two bed sets, the time for each of the seven steps of a $CO_2$ capture bed regeneration half cycle can be as shown in Table 1, below:

TABLE 1

| Step | Time period | Duration |
| --- | --- | --- |
| I | t1 | 6 h-(t2 + t3) |
| CnD | t2 | 5 min |
| IH | t3 | 30-60 min |
| HV | t4 | 5 min |
| HP | t5 | 5-30 min |
| CP | t6 | 30-60 min |
| I | t7 | 6 h-(t4 + t5 + t6) |

While the capture bed C2 is undergoing the FI, CnD, IH, HV steps, there is no inflow to the bed. As such, at least a portion of the dry and low $CO_2$ content gas leaving the capture bed C1 via valve V13 (e.g., that portion not blended with product $CO_2$ at stream 3) during this portion of the cycle can pass through valve V18 (valves V17, V22 and V23 closed), bypassing the $CO_2$ capture bed C2 to enter desiccant bed D2 through valve V8 (valve V6 closed) in countercurrent direction relative to feed to initiate regeneration of desiccant bed D2. The humid air stream 2 leaves desiccant bed D2 through valve V4 (valve V2 closed) and leaves the system through valve V20, e.g., a vent stream to ambient air.

During the CnD step, $CO_2$ bed C2 reaches the lowest pressure of the cycle, with gas being removed from the bed through valve V12 (valves V10, V11, V14 and V16 closed) and then through valve V21 (valves V19 and V22 closed) using a vacuum pump 34, thereby creating exhaust to ambient air stream 8 that will primarily include $CO_2$ depleted air from the void spaces in $CO_2$ capture bed C2.

Following the CnD step, and during the IH step, $CO_2$ capture bed C2 remains closed while heated, e.g., via electrical heater 30 to the targeted temperature e.g., from about 50° C. to about 80° C., from about 70° C. to about 100° C., from about 90° C. to about 120° C., from about 110° C. to about 140° C., from about 130° C. to about 160° C., from about 150° C. to about 180° C., or from about 170° C. to about 200° C. in some examples, causing $CO_2$ to desorb and the bed to pressurize to the maximum pressure of the cycle. During the following HV step, the hot dry and $CO_2$ rich gas coming from $CO_2$ capture bed C2 can leave the bed C2 through valve V12 (valves V10, V14 and V16 closed) and can be sent, e.g., via a compressor 35 to the storage/delivery tank 32 through valve V19 (valves V21 and V22 closed).

Following the HV step, a purge gas can be used to continue capture of $CO_2$ off of the capture bed C2. Accordingly, during the HP step, dry, hot, and high $CO_2$ content gas coming from $CO_2$ bed C2 still leaves through valve V12 (valves V10 and V14 closed) but also now some of the flow off of the bed C1 can pass through valve V16 to allow some of the dry and low $CO_2$ content gas to enter the bed to assist in bed regeneration and $CO_2$ product production as explained above. The high $CO_2$ content gas leaving through valve V12 during the HP step can still be sent via a compressor 35 to the storage/delivery tank 32 via valve V19 (valves V21 and V22 closed).

During the HP step, a portion of the dry and low $CO_2$ content gas leaving the capture bed C1 via valve V13 and going through valve V18 can continue regeneration of desiccant bed D2 but now a portion of it can also pass through valve V17 (stream 6) and flow controller FC3 to enter $CO_2$ capture bed C2 through valve V16 (valve V14 closed) for regeneration and to continue to produce an enriched $CO_2$ product.

Following removal of $CO_2$ from the capture bed C2 (determined, e.g., via time of flow or on-line $CO_2$ content determination for flow through valve V12, a CP step can be carried out. During the CP step, the dry and low $CO_2$ content gas leaving capture bed C1 via valve V13 can be diverted through valve V23 (valves V17 and V18 closed) creating stream 7 that can be used to cool down regenerated $CO_2$ capture bed C2 through valve V16 (valve V14 closed) and to heat this gas stream. This heated gas stream leaves $CO_2$ capture bed C2 through valve V12 and passes through valve V22 (valves V10, V11, V19 and V21 closed) into desiccant bed D2 through valve V8 (valve V6 closed) for further regeneration of the desiccant bed D2 in the countercurrent direction relative to feed and exits the system into ambient air the same as before leaving through valves V4 and V20.

Figure 4:
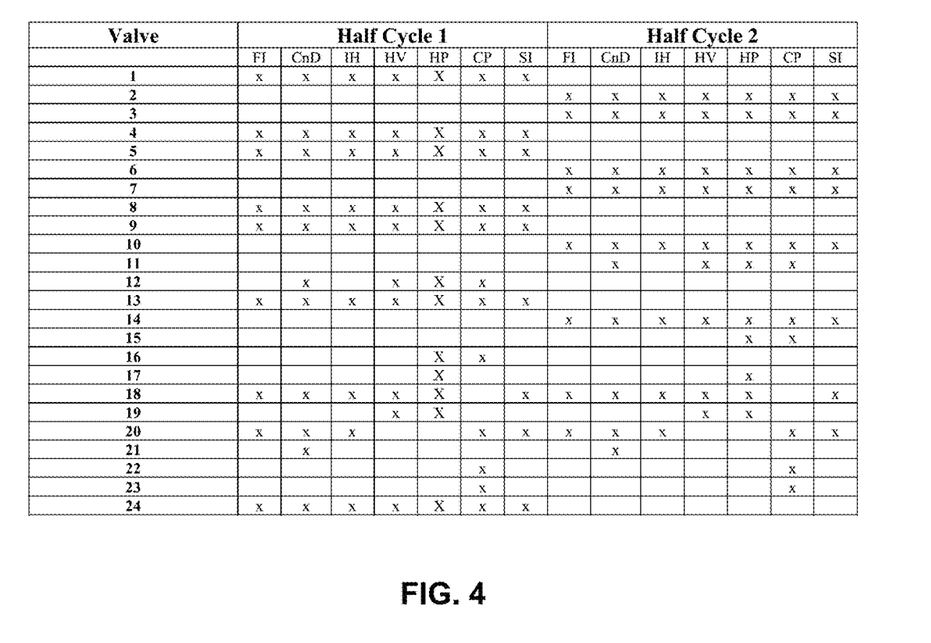
FIG. 4 provides a valve sequence as may be used with the system of FIG. 3 during a single $CO_2$ capture cycle.

Following regeneration of the second set of capture beds D2, C2, these beds can be used to capture $CO_2$ from the feed stream while the first set of beds D1, C1 are regenerated. For instance, during the second 12 hr (night) portion of a 24 hr cycle, the two sets of beds switch roles. During nightlight and depending on the step, valves V2, V3, V6, V7, V10, V11, V14 and V15 are open, valves V1, V4, V5, V8, V9, V12, V13 and V16, are closed, while valves V17, V18, V19, V20, V21, V22, V23 and V24 are open as needed during the regeneration steps. FIG. 4 provides a complete valve sequence as may be utilized in the system illustrated in FIG. 3 in which the regeneration of each capture bed during a half cycle includes seven steps as described. An X in FIG. 4 indicates that the valve of the indicated number is open during that step of the cycle.

Figure 5:
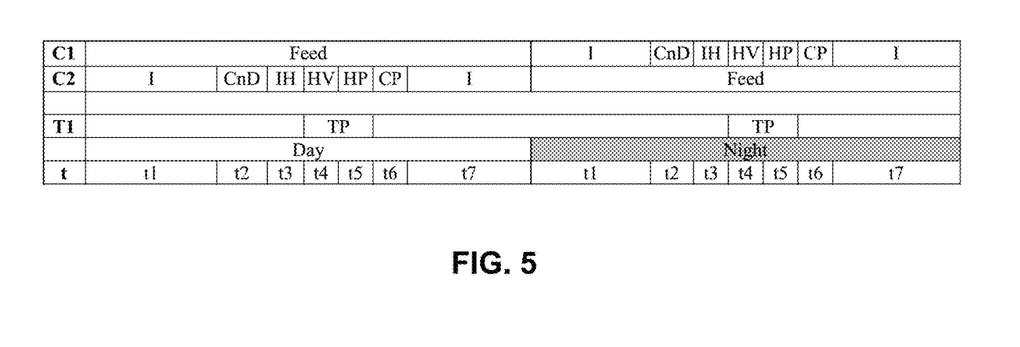
FIG. 5 illustrates a step sequence for two $CO_2$ capture beds over the course of a single cycle of a capture system.

FIG. 5 illustrates an exemplary step sequence for the two capture beds of a two-bed set over the course of a single full cycle. As shown, each bed is regenerated while the other bed is used to capture $CO_2$, and product is pulled off of the capture beds (the tank is pressurized, TP) during the hot venting and hot purging of each capture bed. The time periods for each step t1, t2, t3, etc. can be determined based upon the characteristics of the system and the application of the $CO_2$, among other factors, as discussed previously.

Figure 6:
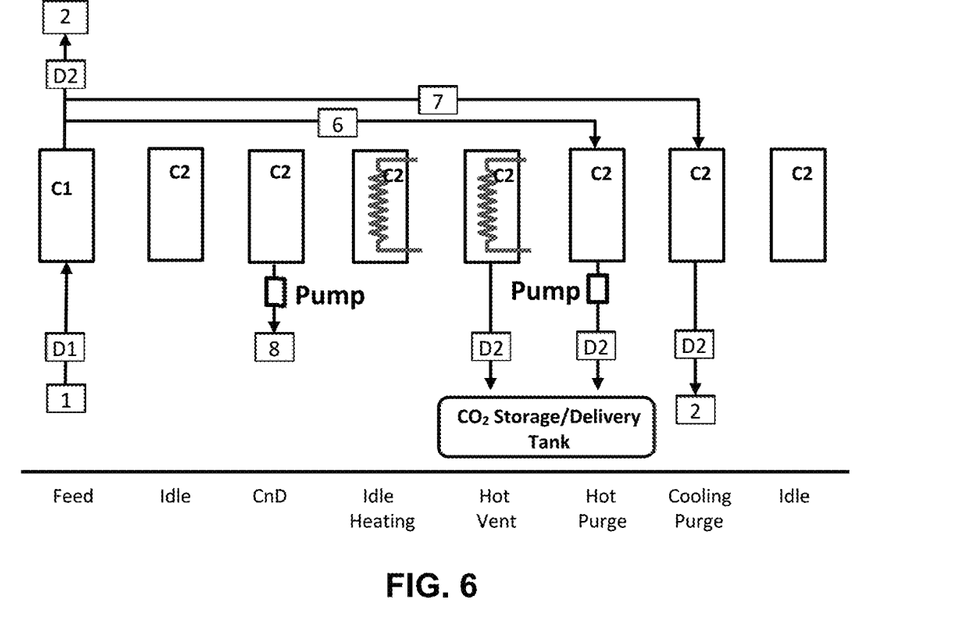
FIG. 6 illustrates a step sequence bed interconnect diagram for two $CO_2$ capture beds.

FIG. 6 schematically illustrates a half cycle step sequence through two $CO_2$ capture beds, and includes an interconnect diagram for the various beds. As shown, the feed stream 1 passes through a desiccant bed D1 and into a capture bed C1 during the C1 Feed step. The dry, low $CO_2$ content gas that passes out of the light product end of this capture bed C1 passes through the second desiccant bed D2 (thereby recharging this second desiccant bed) and out of the system as humid flow 2 during at least a portion of the half cycle. A portion of this dry, low $CO_2$ content gas stream that passes out of the light product end of capture bed C1 passes through the second capture bed C2 in a countercurrent flow as HP flow 6, and a portion of this stream also passes through the second capture bed C2 in a countercurrent flow as CP flow 7 during recharge of the second capture bed C2. As shown, the countercurrent flow off of the capture bed C2 can also be used to regenerate the second desiccant bed D2. For instance, one or all of the HV, HP, and CP flows off of the capture bed C2 can be passed through the desiccant bed D2 in a countercurrent flow for recharging of the desiccant bed D2. In the case of the HV and HP flows, the high $CO_2$ content stream can then be sent to the storage/delivery tank and, following depletion of the level of $CO_2$ in the purge stream the humidified, low $CO_2$ content CP stream can simply be vented at stream 2.

Figure 7:
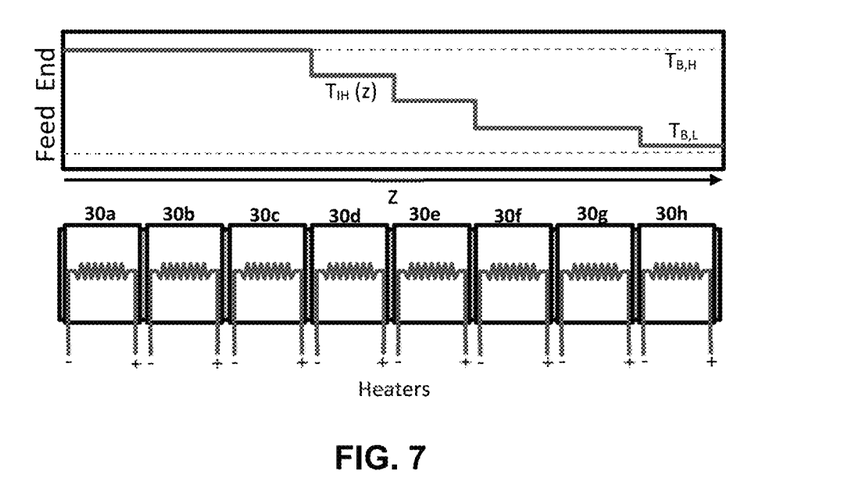
FIG. 7 illustrates an asymmetric bed heating approach as may be used during a $CO_2$ capture bed heating process.

In one embodiment, to further improve efficiency of a system, the heating system used during the heating process of a $CO_2$ capture bed (e.g., the IH step) can include a series of heaters that can be located and controlled so as to obtain reduced energy consumption by a system. For instance, as illustrated in FIG. 7, a series of electric heaters 30a, 30b, 30c, ... 30h. can be located along the length of the bed from the feed end (the feed end of the purge flow, in this case) to the exit (indicated by the arrow z in FIG. 7). The heater nearest the feed end of the bed can be at the highest bed temperature $T_{B,H}$ and the subsequent heaters can be at the same or lower temperature as the bed is dropped to a lowest bed temperature $T_{B,L}$ of the IH step. Of course, the particular temperatures of each heater as well as the heating pattern along the length of the bed can be varied, with preferences depending upon the specific characteristics of the application. Optimization of such a stepped heating approach is well within the capabilities of one of ordinary skill in the art.

Figure 8:
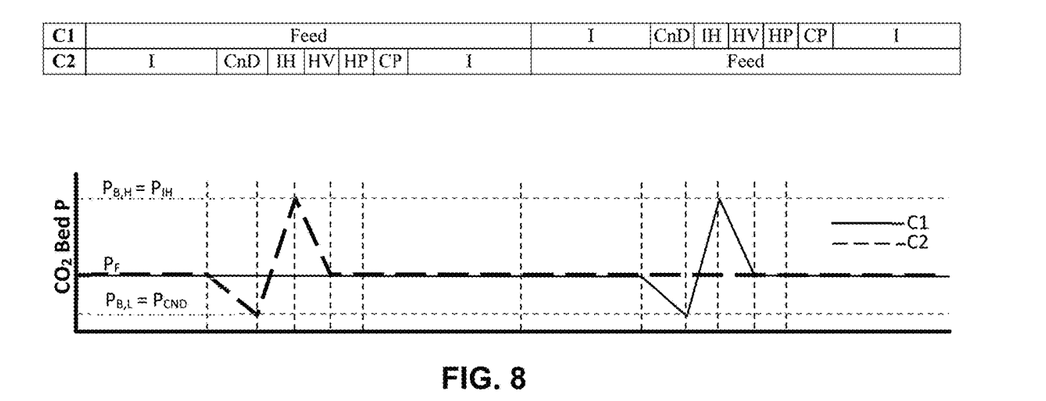
FIG. 8 illustrates the variations in bed pressure for two $CO_2$ capture beds over the course of a single cycle.
Figure 9:
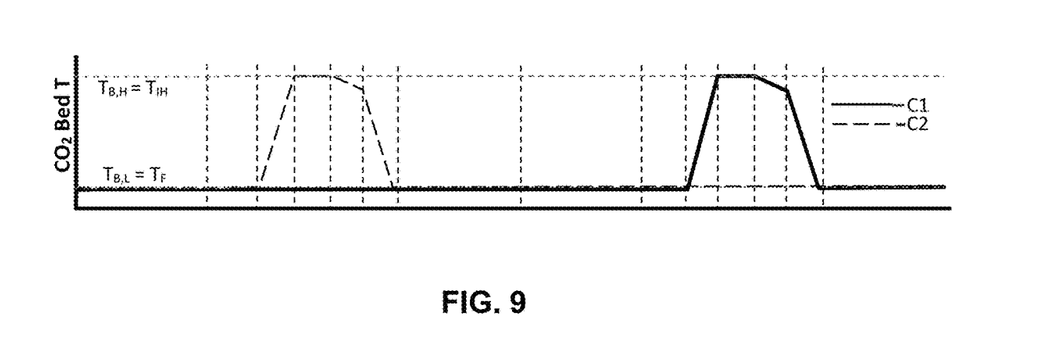
FIG. 9 illustrates the variations in bed temperature for two $CO_2$ capture beds over the course of a single cycle.
Figure 10:
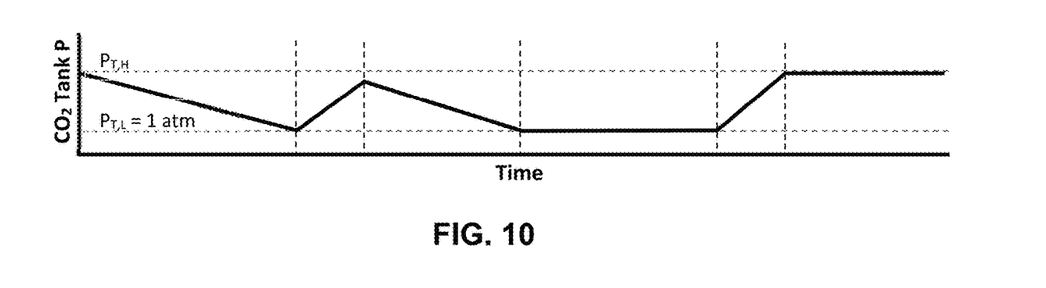
FIG. 10 illustrates the variation in $CO_2$ tank pressure for a $CO_2$ storage tank utilized in one embodiment with a four-bed capture system.

FIG. 8, FIG. 9, and FIG. 10, graphically illustrate the change in capture bed pressure (FIG. 8), capture bed temperature (FIG. 9), and $CO_2$ capture tank pressure of a system such as that illustrated in FIG. 3 over the course of a single full cycle. The seven steps of the regeneration cycle for each bed is shown above the figures and aligned with the figures. As shown in FIG. 8, the pressure of each capture bed will decrease during the CnD step, during which excess low $CO_2$ content gas trapped in the bed is removed, and will increase while the bed is closed and heated as the capture $CO_2$ is desorbed from the bed sorbent material. In accord with the process, the temperature of each bed will increase during the IH step, remain high during the venting and HP step, and then be cooled during the HC step.

In the illustrated embodiment, in which $CO_2$ is removed from the storage tank for delivery to a cultivation pond only during half of the cycle, the tank pressure will decrease during this half cycle and remain stable during the half cycle in which no $CO_2$ is delivered from the tank. As the $CO_2$ is vented and purged from the capture beds, the tank pressure increases during a portion of each half cycle.

The system can operate continuously in such a fashion cycle by cycle, producing in this particular embodiment $CO_2$ for algal pond cultivation from ambient air. Of course, the disclosed systems and methods are not limited to this particular embodiment, and the cyclic system can be scaled up or down and can include multiple different bed sets to fit any size desired $CO_2$ production rate.

While certain embodiments of the disclosed subject matter have been described using specific terms, such description is for illustrative purposes only, and it is to be understood that changes and variations may be made without departing from the spirit or scope of the subject matter.

What is claimed is:

1. A method for separating $CO_2$ from a gaseous stream comprising $CO_2$ and $H_2O$ vapor, the method comprising:
   providing a flow of a feed stream to a first desiccant bed to form a dry gaseous stream;
   providing the dry gaseous stream thus formed to a first $CO_2$ capture bed to form a dry, low $CO_2$ content gas stream;
   providing a first portion of the dry, low $CO_2$ content gas stream to a second desiccant bed, the dry, low $CO_2$ content gas thus provided removing $H_2O$ from the second desiccant bed and regenerating the second desiccant bed;
   providing a second portion of the dry, low $CO_2$ content gas stream to a second $CO_2$ capture bed as a purge gas; and
   regenerating the second $CO_2$ capture bed according to a regeneration process that comprises depressurizing the second $CO_2$ capture bed, heating the second $CO_2$ capture bed following the depressurization, venting the second $CO_2$ capture bed following the heating, purging the second $CO_2$ capture bed by use of the purge gas, and cooling the second $CO_2$ capture bed.

2. The method of claim 1, wherein following purging of the second $CO_2$ capture bed, at least a portion of the purge gas is provided to the second desiccant bed.

3. The method of claim 1, further comprising switching the flow of the feed stream from the first desiccant bed to the second desiccant bed, and upon the switch, regenerating the first desiccant bed and the first $CO_2$ capture bed.

4. The method of claim 1, further comprising collecting $CO_2$ removed from the second $CO_2$ capture bed during the regeneration of the second $CO_2$ capture bed.

5. The method of claim 4, comprising delivery of the collected $CO_2$ to a cultivation area.

6. The method of claim 5, wherein the cultivation area is an algal cultivation pond.

7. The method of claim 6, wherein the collected $CO_2$ is delivered semi-continuously over the course of a day.

8. The method of claim 1, further comprising providing a third portion of the dry, low $CO_2$ content gas stream as a diluent to a high $CO_2$ content gas stream.

9. The method of claim 1, wherein the depressurization of the second $CO_2$ capture bed comprises a countercurrent depressurization.

10. The method of claim 1, wherein the second $CO_2$ capture bed is vented and purged in a countercurrent flow.

11. The method of claim 1, wherein the regeneration of the second $CO_2$ capture bed comprises one or more idle steps.

12. The method of claim 1, wherein the regeneration of the second $CO_2$ capture bed comprises a first idle step, a countercurrent depressurization step, an idle heating step, a hot vent step, a hot purge step, a cooling purge step, and a second idle step.

13. A system for capturing $CO_2$ from a feed gas, the system comprising:
- a first desiccant bed;
- a first $CO_2$ capture bed, wherein a light product end of the first desiccant bed is in controllable communication with a heavy product end of the first $CO_2$ capture bed;
- a second desiccant bed, wherein a light product end of the first $CO_2$ capture bed is in controllable fluid communication with a light product end of the second desiccant bed for countercurrent flow through the second desiccant bed;
- a second $CO_2$ capture bed, wherein the light product end of the first $CO_2$ capture bed is also in controllable fluid communication with a light product end of the second $CO_2$ capture bed for countercurrent flow through the second $CO_2$ capture bed, and wherein
- the light product end of the second desiccant bed is in controllable fluid communication with a heavy product end of the second $CO_2$ capture bed,
- the light product end of the second $CO_2$ capture bed is in controllable fluid communication with the light product end of the first desiccant bed for countercurrent flow through the first desiccant bed, and
- the light product end of the second $CO_2$ capture bed is also in controllable fluid communication with the light product end of the first $CO_2$ capture bed for countercurrent flow through the first $CO_2$ capture bed.

14. The system of claim 13, further comprising a $CO_2$ storage tank in controllable fluid communication with a heavy product end of the first $CO_2$ capture bed and also in controllable fluid communication with a heavy product end of the second $CO_2$ capture bed.

15. The system of claim 13, further comprising a first vacuum pump in fluid communication with a heavy product end of the first $CO_2$ capture bed.

16. The system of claim 15, further comprising a second vacuum pump in fluid communication with a heavy product end of the second $CO_2$ capture bed.

17. The system of claim 13, further comprising a first heater in thermal communication with the first $CO_2$ capture bed and a second heater in thermal communication with the second $CO_2$ capture bed.

18. The system of claim 17, wherein the first and second heaters comprise electric heaters.

19. The system of claim 18, wherein the first heater comprises a series of heaters along a length of the first $CO_2$ capture bed and the second heater comprises a series of heaters along a length of the second $CO_2$ capture bed.

20. The system of claim 13, wherein the first and second $CO_2$ capture beds are in fluid communication with a cultivation area.

* * * * *